US00PP26314P2

(12) United States Plant Patent
Miklósné

(10) Patent No.: US PP26,314 P2
(45) Date of Patent: Jan. 19, 2016

(54) ***PRUNUS* PLANT NAMED 'ANTONIUS'**

(50) Latin Name: *Prunus laurocerasus*
Varietal Denomination: Antonius

(71) Applicant: Józsa Miklósné, Szombathely (HU)

(72) Inventor: Józsa Miklósné, Szombathely (HU)

( * ) Notice: Subject to any disclaimer, the term of this patent is extended or adjusted under 35 U.S.C. 154(b) by 24 days.

(21) Appl. No.: 13/986,501

(22) Filed: May 9, 2013

Related U.S. Application Data

(60) Provisional application No. 61/797,657, filed on Dec. 12, 2012.

(51) Int. Cl.
*A01H 5/08* (2006.01)

(52) U.S. Cl.
USPC ..... Plt./180

(58) Field of Classification Search
USPC ..... Plt./180, 226
CPC ..... A01H 5/0837
See application file for complete search history.

(56) References Cited

PUBLICATIONS

Gabot Dossier Plantarium, 2011.*
Gabot Dossier Plantarium, 2011, translation.*

* cited by examiner

*Primary Examiner* — Keith O. Robinson
(74) *Attorney, Agent, or Firm* — Penny J. Aguirre

(57) ABSTRACT

A new cultivar of *Prunus laurocerasus*, 'Antonius', characterized by its dark green glossy mature leaves and young leaves that are bronze red in color, its upright and narrow plant habit; reaching about 2 m in height and 0.8 m in width, its good disease resistance, and its hardiness at least in U.S.D.A. Zones 6 to 9.

2 Drawing Sheets

Botanical classification: *Prunus laurocerasus*.
Variety denomination: 'Antonius'.

BACKGROUND OF THE INVENTION

The present invention relates to a new and distinct cultivar of *Prunus laurocerasus*, and will be referred to hereafter by its cultivar name, 'Antonius'. 'Antonius' is a new cultivar of cherry laurel grown for use as a landscape plant.

The new cultivar of *Prunus*, 'Antonius', arose from an ongoing breeding program by the Inventor in Szombathely, Hungary. The new cultivar was selected as a naturally occurring whole plant mutation in summer of 2002 that arose from seeds collected, pooled and sown from open pollination of the cultivars 'Mari', 'Piri', and Klàri (all three not patented). The exact parenage is unknown.

Asexual propagation of the new cultivar was first accomplished by stem cuttings by the Inventor in Szombathely, Hungary in September of 2007. Asexual propagation by stem cuttings has determined that the characteristics of the new cultivar are stable and reproduced true to type in successive generations.

SUMMARY OF THE INVENTION

The following traits have been repeatedly observed and represent the characteristics of the new *Prunus*. These attributes in combination distinguish 'Antonius' as a unique cultivar of *Prunus*.

1. 'Antonius' exhibits dark green glossy mature leaves and young leaves that are bronze red.
2. 'Antonius' exhibits an upright and narrow plant habit; reaching about 2 m in height and 0.8 m in width.
3. 'Antonius' exhibits good disease resistance.

4. 'Antonius' exhibits good hardiness with hardiness at least in U.S.D.A. Zones 6 to 9.

'Antonius' is unique and unlike any other cultivars of *Prunus laurocerasus* known to the Inventor. Possible parent plants; 'Mari', 'Piri', and Klàri, all differ from 'Antonius' in having green young foliage, in lacking glossy leaves, and in having a mounded plant habit. 'Antonius' can be most closely compared to the cultivars 'Anbri' (not patented) and 'Otto Luyken' (not patented). 'Anbri' is similar to 'Antonius' in having young leaves that are bronze red in color and mature leaves that are glossy and dark green in color, however 'Anbri' differs from 'Antonius' in having leaves that are less elongated and in having a mounded plant habit. 'Otto Luyken' is similar to 'Antonius' in having glossy dark green mature leaves, but differs from 'Antonius' in having young foliage that is green in color and in having a shorter plant height (about 1 m in height when grown under the same conditions).

BRIEF DESCRIPTION OF THE DRAWING

The accompanying colored photographs illustrate the overall appearance and distinct characteristics of the new cultivar. The photographs were taken of a 6 year-old plant as grown outdoors in a trial bed in Szombathely, Hungary.

The photograph in FIG. 1 illustrates the plant habit of 'Antonius'.

Figure 1:
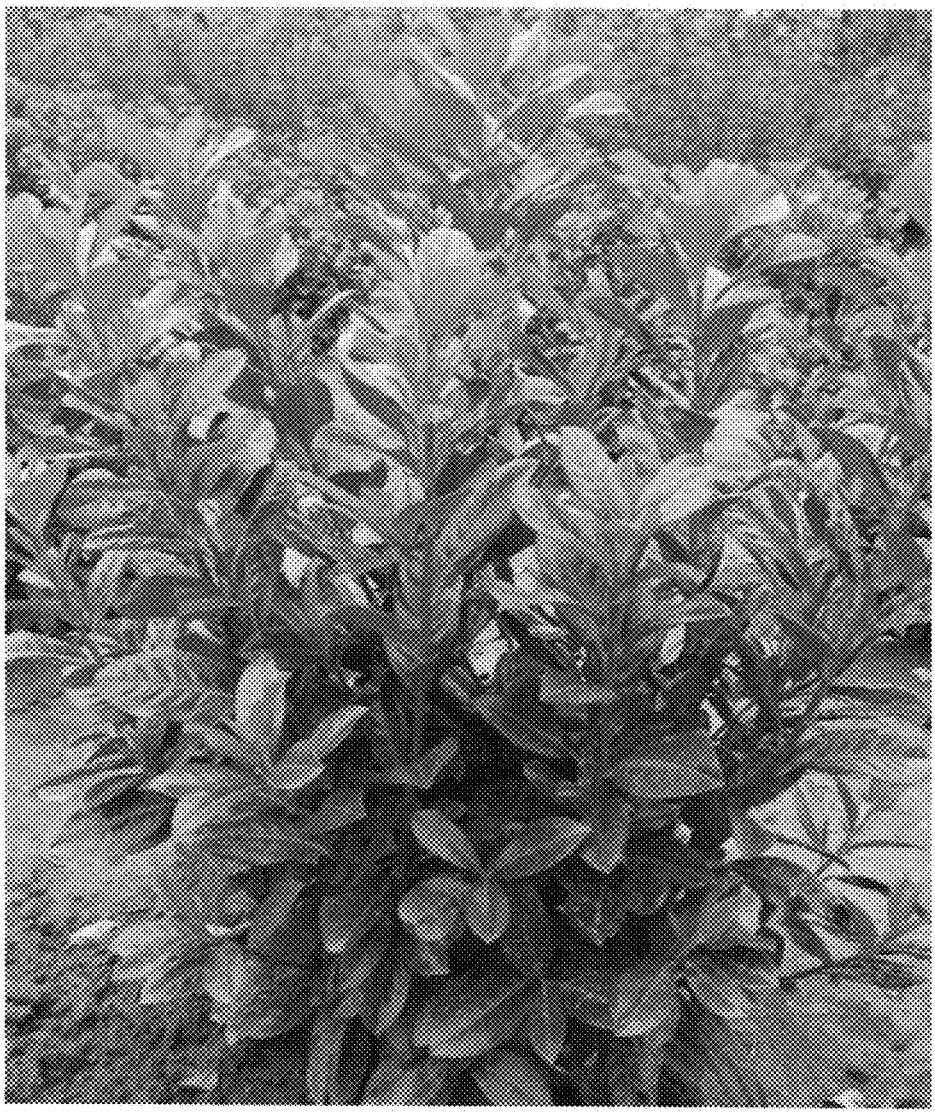
Figure 2:
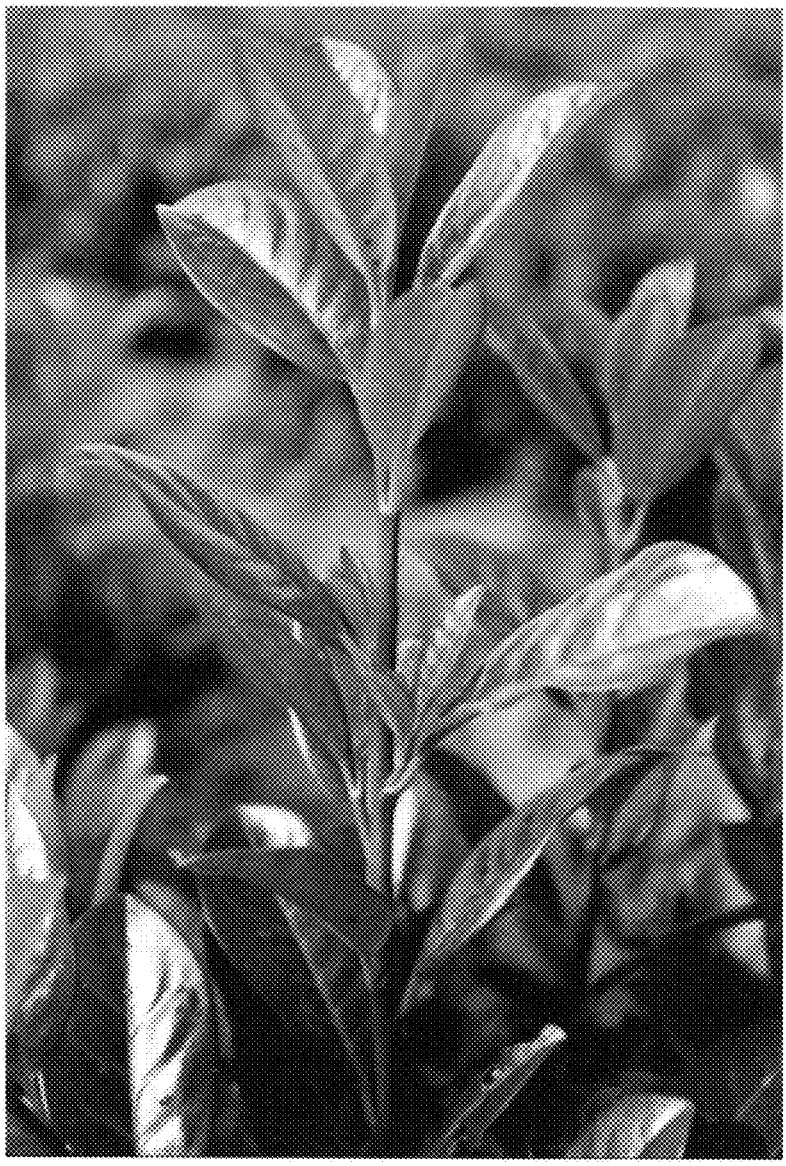

The photograph in FIG. 2 is a close-up view of young and mature leaves of 'Antonius'.

The colors in the photographs are as close as possible with the digital photography techniques available, the color values cited in the detailed botanical description accurately describe the colors of the *Prunus*.

DETAILED BOTANICAL DESCRIPTION

The following is a detailed description of 6 year-old trees of the new cultivar as grown outdoors in a trial bed in Szombathely, Hungary. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Evergreen shrub.

*Plant habit.*—Narrow and upright.

*Height and spread.*—Reaches about 2 m in height and about 0.8 m width.

*Hardiness.*—At least in U.S.D.A. Zones 6 to 9.

*Diseases and pests.*—Has been shown to have good resistance to powdery mildew (caused by *Podosphaera clandestine*) and leaf spot (caused by *Cercospora* spp. Fresen).

*Root description.*—Fleshy, color primarily 199A.

*Propagation.*—Stem cuttings.

*Root initiation.*—4 to 6 weeks in a greenhouse in autumn.

*Root development*.—Autumn rooted cuttings fully develop in a liner in 45 days at 20° to 25° C. during the summer.

*Growth rate.*—Moderate.

Stem description:

*Shape.*—Slightly oval.

*Stem color*.—New growth; 144B to 144C and suffused with 172C, mature stems; 144B, old wood; N199B.

*Branching.*—5 to 7 main stems and 15 to 17 lateral braches per main stem with an average angle of 15° to 20° to vertical.

*Stem size.*—Main stems; 0.6 to 0.7 m in length and 2 cm in diameter, lateral branches range from 25 to 30 cm in length and 0.6 to 0.8 cm in diameter.

*Stem surface.*—Young stems glabrous with slight glossy, mature stems glabrous.

*Branch internode length.*—Average of 8 cm.

*Stem fragrance.*—Emit a cherry aroma if bruised.

*Branch strength.*—Very strong.

Foliage description:

*Leaf shape.*—Elongated elliptic.

*Leaf division.*—Simple.

*Leaf base.*—Cuneate.

*Leaf apex.*—Acute to cuspidate.

*Leaf fragrance.*—None.

*Leaf venation.*—Pinnate, conspicuously recessed on upper surface, color on mature leaves upper and lower surface is 144C.

*Leaf margins.*—Serrated.

*Leaf arrangement.*—Alternate.

*Leaf attachment.*—Petiolate.

*Leaf surface.*—Glabrous and highly glossy on upper and lower surface.

*Leaf size.*—Mature leaves average 7 to 8 cm in length and 3 to 4 cm in width.

*Leaf internodes.*—2 to 3 cm.

*Leaf color.*—Newly expanded leaves upper and lower surface; 172C, mature leaves upper and lower surface 137B to 137C.

*Petioles.*—Average of 1 cm in length and 2 mm in width, 144C in color, glabrous surface.

*Leaf glands.*—Typically 2 per leaf and present near the base on the lower surface of leaf, circular in shape, an average of 1 mm in diameter, 200A in color.

Inflorescence description: Blooms have not been observed.

It is claimed:

1. A new and distinct cultivar of *Prunus* plant named 'Antonius' as herein illustrated and described.

* * * * *